United States Patent
Obermiller et al.

(10) Patent No.: US 8,877,233 B2
(45) Date of Patent: Nov. 4, 2014

(54) POROUS SPONGE MATRIX MEDICAL DEVICES AND METHODS

(75) Inventors: Joseph Obermiller, West Lafayette, IN (US); Michael C. Hiles, Lafayette, IN (US)

(73) Assignee: Cook Biotech Incorporated, West Lafayette, IN (US)

( * ) Notice: Subject to any disclaimer, the term of this patent is extended or adjusted under 35 U.S.C. 154(b) by 0 days.

(21) Appl. No.: 10/184,559

(22) Filed: Jun. 28, 2002

(65) Prior Publication Data

US 2003/0013989 A1    Jan. 16, 2003

Related U.S. Application Data

(60) Provisional application No. 60/302,245, filed on Jun. 29, 2001.

(51) Int. Cl.
  *A61F 13/00* (2006.01)
  *A61K 9/70* (2006.01)
  (Continued)

(52) U.S. Cl.
  CPC .......... *A61L 31/146* (2013.01); *A61B 17/0057* (2013.01); *A61L 27/56* (2013.01); *A61B 17/1219* (2013.01); *A61L 26/0033* (2013.01); *A61L 26/0085* (2013.01); *A61L 31/044* (2013.01); *A61B 10/0233* (2013.01); *A61B 17/12022* (2013.01); *A61B 2017/00637* (2013.01); *A61B 2017/00898* (2013.01); *A61L 2400/04* (2013.01); *A61L 27/24* (2013.01); *A61B 2017/00654* (2013.01); *A61B 2017/00004* (2013.01)

USPC .......... 424/443; 424/445; 424/446; 424/447; 424/423; 623/1.1; 623/1.11; 623/1.12; 604/15; 604/21; 604/57; 604/208; 604/228; 604/311

(58) Field of Classification Search
  USPC ................................... 424/449, 443
  See application file for complete search history.

(56) References Cited

U.S. PATENT DOCUMENTS

| | | | |
|---|---|---|---|
| 3,566,871 | A | 3/1971 | Richter et al. |
| 3,810,473 | A | 5/1974 | Cruz, Jr. et al. |

(Continued)

FOREIGN PATENT DOCUMENTS

| | | |
|---|---|---|
| CA | 2245754 | 3/1999 |
| EP | 0 901 792 A2 | 3/1999 |

(Continued)

OTHER PUBLICATIONS

"Gylosaminoglycans and the regulation of blood coagulation" Biochem. J. (1993) 289, 313-330.*

(Continued)

*Primary Examiner* — Isis Ghali
(74) *Attorney, Agent, or Firm* — Woodard, Emhardt, Moriarty, McNett & Henry LLP

(57) ABSTRACT

Described are hemostasis devices useful for implantation in biopsy tracts, which device comprise highly compact, dried hemostatic sponge elements. Preferred devices also include compacted sponge matrices exhibiting high density and rigidity in combination with high volumetric expandability when wetted. Also described are methods for making and using such devices.

33 Claims, 2 Drawing Sheets

(51) Int. Cl.

| | |
|---|---|
| A61L 15/00 | (2006.01) |
| A61L 15/16 | (2006.01) |
| A61F 2/00 | (2006.01) |
| A61F 2/06 | (2013.01) |
| A61F 13/20 | (2006.01) |
| A61N 1/30 | (2006.01) |
| A61M 31/00 | (2006.01) |
| A61M 5/00 | (2006.01) |
| A61M 5/315 | (2006.01) |
| A61M 35/00 | (2006.01) |
| A61B 17/00 | (2006.01) |
| A61L 27/56 | (2006.01) |
| A61B 17/12 | (2006.01) |
| A61L 31/14 | (2006.01) |
| A61L 26/00 | (2006.01) |
| A61L 31/04 | (2006.01) |
| A61L 27/24 | (2006.01) |
| A61B 10/02 | (2006.01) |

(56) References Cited

U.S. PATENT DOCUMENTS

| | | | | |
|---|---|---|---|---|
| 3,823,212 | A | * | 7/1974 | Chvapil .................. 264/49 |
| 4,193,813 | A | | 3/1980 | Chvapil |
| 4,271,835 | A | | 6/1981 | Conn et al. |
| 4,511,653 | A | | 4/1985 | Play et al. |
| 4,578,067 | A | | 3/1986 | Cruz |
| 4,846,793 | A | | 7/1989 | Leonard et al. |
| 4,852,568 | A | | 8/1989 | Kensey |
| 4,902,508 | A | | 2/1990 | Badylak et al. |
| 4,956,178 | A | | 9/1990 | Badylak et al. |
| 4,970,298 | A | * | 11/1990 | Silver et al. .................. 530/356 |
| 5,206,028 | A | * | 4/1993 | Li .................. 424/484 |
| 5,219,576 | A | | 6/1993 | McMullin et al. |
| 5,275,616 | A | | 1/1994 | Fowler |
| 5,279,555 | A | | 1/1994 | Lifshey |
| 5,325,857 | A | | 7/1994 | Nabai et al. |
| 5,388,588 | A | * | 2/1995 | Nabai et al. .................. 600/567 |
| 5,391,183 | A | | 2/1995 | Janzen et al. |
| 5,394,886 | A | | 3/1995 | Nabai et al. |
| 5,449,375 | A | | 9/1995 | Vidal et al. |
| 5,456,693 | A | * | 10/1995 | Conston et al. .................. 606/192 |
| 5,467,780 | A | | 11/1995 | Nabai et al. |
| 5,479,936 | A | | 1/1996 | Nabai et al. |
| 5,483,972 | A | | 1/1996 | Nabai et al. |
| 5,532,221 | A | * | 7/1996 | Huang et al. .................. 514/53 |
| 5,554,389 | A | | 9/1996 | Badylak et al. |
| 5,571,181 | A | * | 11/1996 | Li .................. 623/23.75 |
| 5,674,298 | A | | 10/1997 | Levy et al. |
| 5,782,914 | A | | 7/1998 | Schankereli |
| 6,008,292 | A | | 12/1999 | Lee et al. |
| 6,056,970 | A | * | 5/2000 | Greenawalt et al. .................. 424/426 |
| 6,071,301 | A | * | 6/2000 | Cragg et al. .................. 606/213 |
| 6,099,567 | A | | 8/2000 | Badylak et al. |
| 6,130,264 | A | | 10/2000 | Cercone et al. |
| 6,183,497 | B1 | | 2/2001 | Sing et al. |
| 6,190,350 | B1 | | 2/2001 | Davis et al. |
| 6,206,931 | B1 | | 3/2001 | Cook et al. |
| 6,261,309 | B1 | | 7/2001 | Urbanski |
| 6,270,464 | B1 | | 8/2001 | Fulton, III et al. |
| 6,371,904 | B1 | | 4/2002 | Sirimanne et al. |
| 6,379,710 | B1 | | 4/2002 | Badylak |
| 6,536,782 | B2 | | 3/2003 | Rohm |
| 6,541,031 | B1 | | 4/2003 | Beisel |
| 6,605,047 | B2 | | 8/2003 | Zarins et al. |
| 6,699,205 | B2 | | 3/2004 | Fulton, III et al. |

FOREIGN PATENT DOCUMENTS

| | | | |
|---|---|---|---|
| EP | 1022031 | 7/2000 | |
| EP | 1022031 A1 * | 7/2000 | .............. A61L 15/32 |
| GB | 887844 | 1/1962 | |
| WO | WO 98/09617 A1 | 3/1998 | |
| WO | WO 98/22158 | 5/1998 | |
| WO | WO 98/25637 | 6/1998 | |
| WO | WO 00/32250 | 6/2000 | |
| WO | WO 00/32250 A1 * | 6/2000 | |
| WO | WO 01/13800 | 1/2001 | |

OTHER PUBLICATIONS

Chan-Myers, HB, et al. "Sterilization of a Small Caliber Vascular Graft with a Polyepoxy Compound". *ASAIO Journal*, 1992. vol. 38, pp. 116-119. Lippincott Williams & Wilkins, United States.

Fandrich, CA, et al. "Small Gauge Gelfoam Plug Liver Biopsy in High Risk Patients: Safety and Diagnostic Value". *Australasian Radiology*, Aug. 1996. vol. 40, No. 3. pp. 230-234. Blackwell Scientific Publications, Australia.

Kallmes, DF, et al. "In Vivo Evaluation of a New Type I Collagen Hemostatic Plug for High-Risk, Large-Core Biopsies". *Journal of Vascular and Interventional Radiology*, Jul.-Aug. 1998. vol. 9, No. 4. pp. 656-659. Society of Cardiovascular and Interventional Radiology, United States.

Kaufman, R, et al. "Hair Transplantation: Gelatin Plugs for Hemostasis". *Z Hautkr*, Aug. 1983. vol. 58, No. 15. pp. 1139-1141. Grosse, Germany.

Lohre, JM, et al. "Evaluation of Two Epoxy Ether Compounds for Biocompatible Potential". *Artificial Organs*, Dec. 1992. vol. 16, No. 6. pp. 630-633. Blackwell Science, United States.

Lohre, JM, et al. "Evaluation of Epoxy Ether Fixed Bovine Arterial Grafts for Mutagenic Potential". *ASAIO Journal*, Apr.-Jun. 1993. vol. 39, No. 2, pp. 106-113. Lippincott Williams & Wilkins, United States.

Robinson, JD, et al. "The Biocompatibility of Compressed Collagen Foam Plugs". *Cardiovascular and Interventional Radiology*, Feb.-Mar. 1990. vol. 13, No. 1. pp. 36-39. Springer Verlag, United States.

Skelton, HG, et al. "Helistat Absorbable Collagen Hemostatic Sponges in Cutaneous Surgery in HIV-1+ Patients." Military Medical Consortium for the Advancement of Military Medicine (MMCAR). *International Journal of Dermatology*, Nov. 1993. vol. 32, No. 11. pp. 835-837. Decker Periodicals, United States.

Smith, KJ, et al. "Bovine Collagen Products and Gelatin Sponges for Hemostasis in Punch Biopsies of HIV-1+ Patients". *Dermatologic Surgery*, Jun. 1995. vol. 21, No. 6. pp. 563-564. Blackwell Science, United States.

Sung, HW, et al. "Comparison of the Cross-Linking Characteristics of Porcine Heart Valves Fixed with Glutaraldehyde or Epoxy Compounds". *ASAIO Journal*, Jul.-Sep. 1993. vol. 39, No. 3, pp. 532-536. Lippincott Williams & Wilkins, United States.

Tang, Z, et al. "Crosslinkage of Collagen by Polyglycidyl Ethers". *ASAIO Journal*, 1995. vol. 41, pp. 72-78. Lippincott Williams & Wilkins, United States.

Zhou, J., et al. "Porcine Aortic Wall Flexibility. Fresh vs. Denacol Fixed vs. Glutaraldehyde Fixed". *ASAIO Journal*, Sep.-Oct. 1997. vol. 43, No. 5, pp. 470-475. Lippincott Williams & Wilkins, United States.

Robinson, JD et al, "The Biocompatibility of Compressed Collagen Foam Plugs", Cardiovascular and Interventional Radiology, Feb.-Mar. 1990. vol. 13, No. 1. pp. 36-39. Springer Vertag, United States.

* cited by examiner

POROUS SPONGE MATRIX MEDICAL DEVICES AND METHODS

REFERENCE TO RELATED APPLICATION

This application claims the benefit of U.S. Provisional Patent Application Ser. No. 60/302,245 entitled POROUS SPONGE MATRIX MEDICAL DEVICES AND METHODS filed Jun. 29, 2001, which is hereby incorporated by reference herein in its entirety.

BACKGROUND

The present invention relates generally to medical devices and methods. In one particular aspect, the invention relates to porous sponge matrix devices and materials which are medically useful, for example, to facilitate hemostasis when applied to or within patient tissues.

As further background, sponge matrix devices have found wide application in the medical (including veterinary) fields. Among other things, sponge matrices have been used to provide hemostasis, and to serve as substrates and/or scaffolds in the delivery of therapeutic chemicals, proteins, nucleic acids or cells to patients.

In one facet of medicine, tissue biopsies are often taken from suspect tissue for diagnostic purposes. A wide variety of core biopsy devices and methods have been proposed, all of which typically excise a volume of tissue from the patient. Such procedures can lead to internal bleeding within the biopsied tissues, both due to the removal of tissue and to the needle tract created to extend the sampling portion of the device to the tissue site from which the biopsy is needed.

In current clinical practice, no measures are taken to try to stop or slow the internal bleeding, and the body is simply allowed to undertake its natural clotting and healing processes. This is perhaps due to the difficulties in treating the affected areas, which are often located in relatively deep tissue of the patient.

Needs exist generally in the medical field for devices, materials and methods for providing treatment of patient tissues, for example tissues from which biopsy samples have been obtained. Such devices, materials and methods, as utilized to treat biopsied tissues, would desirably minimize any further procedure or discomfort to the patient, and would be relatively simple to use. The present invention addresses these needs.

SUMMARY OF THE INVENTION

In one aspect, the present invention provides medical devices that include a dry sponge matrix material in a compressed configuration. The preferred sponge matrix material of the invention defines pores and is stabilized in a compressed state, for example by drying the sponge matrix material in a compressed state. The preferred material is highly dense and compact when dry, but expands substantially when wetted. For example, in advantageous embodiments, the inventive compressed matrix material expands at least 100% by volume when wetted. The sponge matrix material desirably has a density, in its compacted, dry state, of at least about 0.05 g/cm$^3$. The preferred matrix material is crosslinked, desirably with a polar crosslinking agent that imparts a hydrophilic character to the matrix material thus improving its wettability. Suitable crosslinking agents for these purposes include for instance polyepoxide compounds such as polyglycidyl ethers.

In preferred embodiments of the invention, the compacted or compressed sponge matrix material of the invention is incorporated in percutaneously-deliverable medical devices. Such devices are advantageously sized and configured for passage through needle and/or catheter cannulas. For example, the present invention provides a hemostasis device which comprise a compacted, dry sponge matrix, wherein the device is sized for deployment through a cannula, for example a cannula of a diameter consistent with a core biopsy needle and/or associated catheter.

In another aspect, the invention provides a method for preparing an expandable sponge matrix, which comprises providing a hydrated or otherwise wetted, porous sponge matrix, and drying the material under compression. Drying can be conducted, for instance, by freeze drying or vacuum drying the sponge matrix. Compression forces may be applied in one dimension or multiple dimensions during the drying process.

The invention also provides a method for treating a patient which comprises implanting in the patient a medical device including a compressed sponge matrix of the invention as described above. In a preferred mode, this method provides hemostasis in a biopsy site from which a biopsy tissue sample has been taken.

The invention also provides a tissue biopsy method that includes inserting a cannula (such as a needle cannula) to extend to a tissue site for biopsy, the cannula having an associated cutting member for cutting a sample of tissue from the tissue site. The cutting member is used to cut the sample of tissue, which is extracted from the patient through the cannula. The method also includes delivering to the tissue site through the cannula a hemostatic element formed from a dry sponge matrix stabilized in a compressed configuration and expansible when wetted.

The present invention provides improved medical devices including sponge matrices which can be used for example in providing hemostasis, and methods for preparing and using the matrices and devices. Additional objects, features and advantages of the invention will be apparent from the descriptions herein.

DESCRIPTION OF PREFERRED EMBODIMENTS

Figure 1:
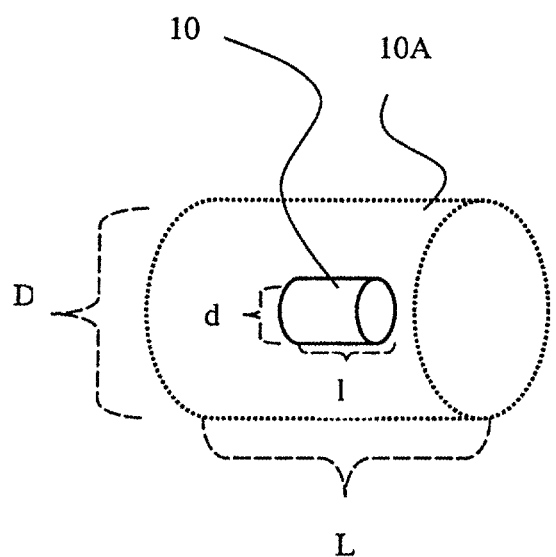
FIG. 1 provides a perspective view of a hemostatic sponge pellet device of the invention.

For the purpose of promoting an understanding of the principles of the invention, reference will now be made to certain preferred embodiments thereof and specific language will be used to describe the same. It will nevertheless be understood that no limitation of the scope of the invention is thereby intended, such alterations, further modifications and applications of the principles of the invention as described herein being contemplated as would normally occur to one skilled in the art to which the invention relates.

As disclosed above, the present invention provides medical sponge matrices which are useful inter alia in hemostasis implant devices. Preferred such devices include compact, dry, sponge elements configured for deployment through a cannula to a biopsy site. The invention also provides methods for using such devices and matrices in the treatment of patients, for example for treatment of biopsied sites. Further, the invention provides methods for preparing highly compact and dense sponge matrices which involve compressing sponge matrices while hydrated, and drying the matrices in their compressed state.

Sponge matrices in accordance with the invention will generally comprise porous, three-dimensionally stable bodies formed from suitable biocompatible matrix materials. For example, suitable biocompatible matrix materials include naturally-occurring polymers and/or synthetic polymers. More preferred sponge compositions of the invention will comprise collagen as a matrix-forming material, either alone or in combination with one or more other matrix forming materials. In general, sponge matrices of the invention can be formed by providing a liquid solution or suspension of a matrix-forming material, and causing the material to form a porous three-dimensionally stable structure. Other methods are known and can be used within the scope of the present invention.

Illustratively, in the formation of a collagen sponge, a collagen solution can be prepared. The collagen may be derived from mammalian or other animal sources, for example, bovine, porcine or human sources. Synthetically-derived collagen may also be used. The determination of suitable collagen concentrations in the solution will be within the purview of those skilled in the art, with concentration ranges of about 0.05 g/ml to about 0.2 g/ml being typical.

Digestion of the collagen to form the collagen solution is usually carried out under acidic conditions, starting with ground, minced or otherwise comminuted collagen-containing tissue. Optionally, enzymatic digestion may be utilized using known enzymes for this purpose such as pepsin, trypsin, and/or papain. After digestion, the enzymes can be removed by suitable, known techniques.

In further preparative steps, the collagen solution is treated with a precipitating buffer solution to neutralize the pH and precipitate the collagen. This precipitation can occur during incubation over several hours or days. The resulting product can be dried directly, but is preferably crosslinked with a suitable crosslinking agent and then dried. Illustrative crosslinking agents for these purposes include glutaraldehyde, formaldehyde, carbodiimides, UV irradiation, or other crosslinking agents. In preferred embodiments of the invention, the crosslinking agent will contain polar groups that impart a hydrophilic character to the final sponge matrix material. Desirably, a polyepoxide crosslinker is utilized for this purpose, especially a polyglycidyl ether compound. Suitable such compounds include ethylene glycol diglycidyl ether, available under the trade name Denacol EX810 from Nagese Chemical Co., Osaka, Japan, and glycerol polyglycidyl ether available under the trade name Denacol EX313 also from Nagese Chemical Co. Typically, polyglycidyl ethers or other polyepoxide compounds utilized in the invention will have from 2 to about 10 epoxide groups per molecule. The use of such epoxides and/or other crosslinking agents which impart polar groups and a hydrophilic character to the resulting matrix will provide for good wettability and rapid hydration and expansion of hemostasis devices of the invention.

Preferred sources of collagen for use in the sponge matrices of the invention include extracellular matrix materials such as collagenous submucosal tissues, and other collagenous basement membrane materials. These include, for example, small intestinal submucosa (SIS), stomach submucosa, urinary bladder submucosa, liver basement membrane, and other basement membrane materials. For additional information as to these collagenous matrix materials and their preparation, reference can be made for example to U.S. Pat. Nos. 4,511,653, 4,902,508, 4,956,178, 5,554,389, and 6,099,567, and International Publication Nos. WO9825637 and WO9822158, each of which is hereby incorporated herein by reference in its entirety. In forming sponge matrices of the invention, these materials are preferably processed and utilized under conditions which retain their favorable growth properties. This may include, for example, processing under conditions in which native proteins and/or other materials, for instance biotropic agents, are retained in their bioactive form. For example, the collagen sources, and resulting sponge matrices, may include active native substances such as one or more growth factors, e.g. basic fibroblast growth factor (FGF-2); transforming growth factor beta (TGFss); epidermal growth factor (EFG); platelet derived growth factor (PDGF); and/or other substances such as glycosaminoglycans (GAGs); and/or fibronectin (FN).

With reference to FIG. 1, in one embodiment of the invention, compact sponge matrices of the invention will be used in forming percutaneously-implantable medical devices. For example, the matrices may be used to provide a small sponge element such as a pellet 10 that is useful for implantation into biopsied tissues to facilitate hemostasis and/or to deliver agents. For deployment, sponge element 10 of the invention will be highly compacted and configured for passage through the cannula of a needle and/or a catheter such as that used to obtain core biopsies. Preferred sponge pellets of the invention will have compacted sizes having diameters "d" preferably less than about 2 millimeters so as to be deployable through a needle of corresponding size, e.g. a needle of size 6 French or smaller. Illustrative lengths "1" for sponge pellets of this diameter are less than about 3 centimeters, typically in the range of about 0.25 to about 3 centimeters. These diameters and lengths may of course be varied to suit a particular patient need.

Preferred dry, compressed sponge matrices (and devices formed therefrom) will be highly dense, typically having densities of at least about 0.05 g/cm$^3$, preferably in the range of about 0.05 g/cm$^3$ to about 0.2 g/cm$^3$, and more preferably about 0.075 g/cm$^3$ to about 0.2 g/cm$^3$. The preferred compacted sponge matrix will have sufficient rigidity to be deployed by passage through needles or catheters as discussed above, for example by utilizing a pusher rod or other pusher element to force the sponge matrix device through the needle and/or catheter cannula. Expanded sponge densities (dry) will generally be less than the corresponding compacted densities. Typical expanded densities (dry) will range from about 0.01 g/cm$^3$ to about 0.1 g/cm$^3$, more preferably about 0.02 g/cm$^3$ to about 0.07 g/cm$^3$.

Sponge matrix materials of the invention will advantageously be highly expandable when wetted, so as to achieve an expanded configuration (see 10A, FIG. 1). Preferred sponge materials will exhibit the capacity to expand at least 100% by volume, more preferably at least about 200% by volume, and typically in the range of about 300% by volume to about 1000% by volume, when wetted to saturation with deionized water. Preferred sponge materials of the invention will also exhibit advantageous rates of expansion, achieving volume expansions as noted above in less than about 10 seconds, more preferably less than about 5 seconds, when immersed in deionized water.

The expanded sizes typical for hemostatic sponge pellets of the invention include diameters "D" of about 0.5 cm to about 3 cm, and lengths "L" of about 0.5 cm to 3 cm. Such levels of expansion and final sizes are expected to exert compression on surrounding tissues when implanted, so as to benefit the patient by providing a hemostatic effect within the biopsied tissue. Alternatively or in addition, the pellets may deliver active agents to the implantation site and surrounding tissue.

Highly compact, dense sponge matrices of the invention can be prepared by first hydrating or otherwise wetting a porous sponge matrix, and then compressing and drying the element. Such preparative processes generally provide a more dense, rigid and stably compressed sponge matrix than processes such as simple compaction of the dry sponge matrix. Drying will be conducted sufficiently to stabilize the sponge matrix. For example, preferred drying procedures will reduce the liquid (e.g. water) content of the matrix to less than about 20% by weight, more preferably less than about 10% by weight. Compression forces will be applied so as to achieve a final density and/or configuration desired, and can be applied in one, two or three dimensions, including radially. For example, a sponge pellet prepared from the inventive matrices can have a generally cylindrical shape having a circular or multi-sided (e.g. square or rectangular) cross section, and can have a diameter approximating that or smaller than that of the needle and/or catheter cannula through which it is to be passed. The drying of the compacted element can involve lyophilization (or freeze drying) or vacuum drying at ambient or elevated temperatures. When processed in this fashion, upon removal of the compaction force, the sponge matrix is stabilized structurally and remains in its highly dense and compacted state until contacted with a liquid susceptible to absorption by the matrix, for example body fluids. The pores of the matrix are thereby stably retained at a volume substantially reduced from their maximum volume, but return to a partially or fully expanded state when the matrix material is wetted.

Sponge elements or other devices of the invention may be formed individually by compaction/drying of an appropriately sized sponge element, or they may be individually excised from a larger compacted/dried sponge matrix.

For medical use, the compacted or compressed sponge matrix device can be sterilized using any suitable means, including for example radiation. The device will be suitably packaged in sterile packaging for medical use, to form medical articles of the invention. In this regard, products of the invention may include biopsy kits containing at least one needle for obtaining a biopsy, and at least one sponge pellet of the invention. Suitable biopsy devices including needles include for example Quick-Core® biopsy needles or Twist-Core® biopsy needles available from Cook Diagnostic & Interventional Products.

Figure 2A:
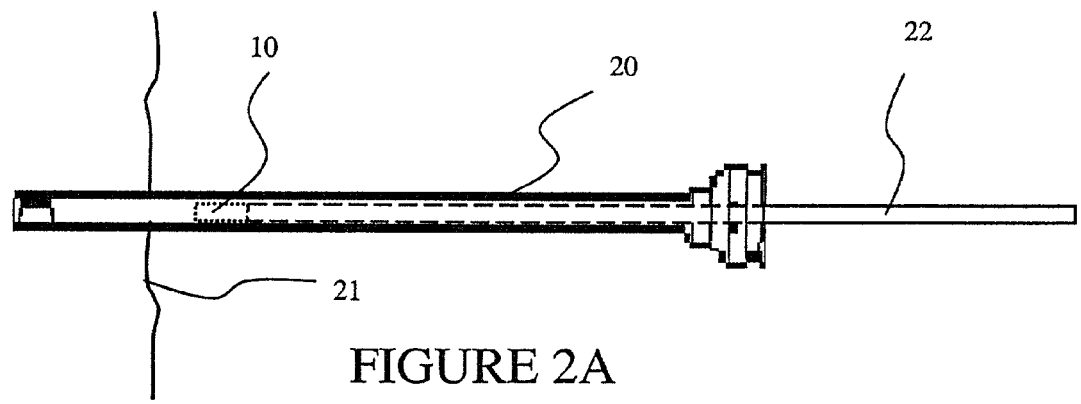
FIGS. 2A-2C provide cross-sectional views of various stages during the implantation of a compressed sponge pellet device of the invention.
Figure 2B:
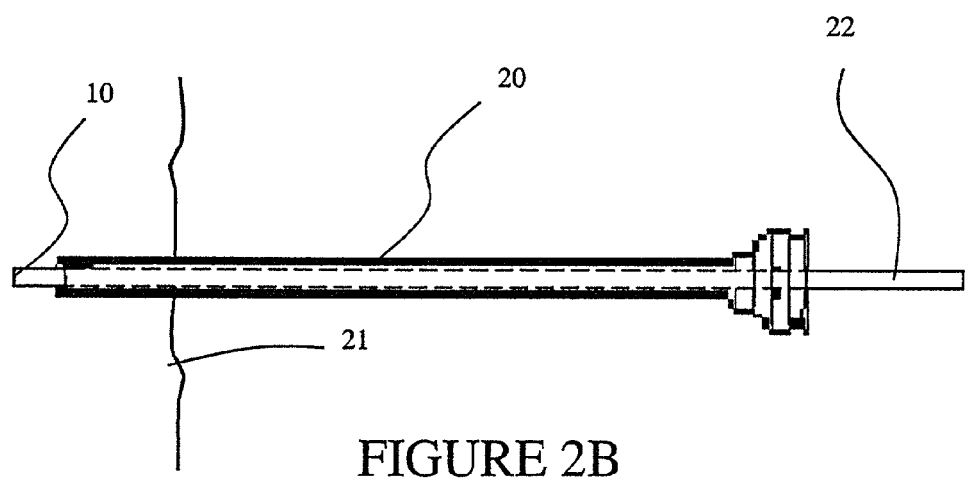
Figure 2C:
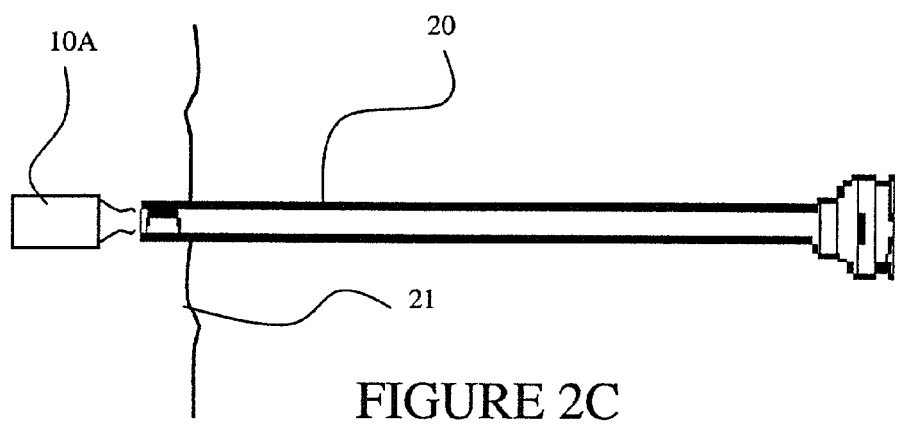

In use in a biopsy procedure, after a core biopsy has been obtained, sponge elements of the invention are implanted into the biopsy site, for instance including the site of the excised tissue and/or the needle tract from the biopsy procedure. Implantation of the sponge element can be achieved through a cannula disposed within the biopsy needle tract. With reference now to FIGS. 2A-2C, in a preferred method, the biopsy procedure is performed with a biopsy device including an outer cannula 20 and an inner sampling needle (not shown). The inner sampling needle is used to obtain the biopsy tissue from the target patient tissue area 21 and withdrawn from the outer needle cannula, which is left in place. Thereafter, a sponge element 10 of the invention can be passed through the outer cannula (FIG. 2A), for example using a rod 22 or other device or mechanism to force the sponge element through the outer cannula and out an opening thereof (FIG. 2B). If desired, multiple sponge elements can be delivered to a single biopsy site. After placement of the sponge element or elements of the invention, the outer cannula can be withdrawn (FIG. 2C), leaving the sponge devices in place in the affected tissue.

Sponge elements or other devices of the invention may also contain one or more active agents therapeutic to the patient. For example, they may include proteins or other substances which promote clotting, for example Thrombin and/or Fibrinogen. Alternatively or in addition, sponge elements or other devices of the invention may include local anesthetics to be delivered to the affected (e.g. biopsied) tissue, and/or growth factors to promote tissue growth and healing within the affected tissue. Illustratively, such active agents can be included in the liquid used to wet the sponge prior to compression.

Sponge elements of the invention may also contain agents which promote further retention of the compressed, high density form of the elements. These may include for example starch, cellulose, sugars such as dextrose, or glycerin. Such agents can optionally be included in the liquid (preferably aqueous) used to hydrate or otherwise wet the sponge prior to compaction and drying.

For the purpose of promoting the further understanding of the present invention and its advantages, the following specific examples are provided. It will be understood that these examples are illustrative and not limiting of the invention.

EXAMPLE 1

Fifty grams of SIS tissue, cut into two-centimeter length pieces, are added to 200 milliliters of a 0.1% pepsin in 0.5 M aqueous acetic acid solution. The resulting preparation is incubated at 37° C. for about 48 hours with stirring. Optionally, any undigested material at that point may be removed by centrifugation at 12,000 RPM for 20 minutes at room temperature. The gelled preparation is dialyzed (molecular weight cutoff of 3500) against several changes of phosphate buffered saline (pH 7.4) over 48 hours at 4° C. The gelled solution is then stored at 4° C. until ready for use. The chilled SIS gel is spread into a mold of desired shape and submersed in a collagen crosslinking solution. The crosslinking solution contains 2% vol/vol diglycidyl ether plus 20% vol/vol ethanol solution at 4° C. for 3-6 days. The resulting crosslinked SIS forms are removed from the crosslinking solution and frozen in a −80° C. freezer. The frozen SIS forms are then lyophilized over a period of approximately 8 hours. The SIS forms are then soaked in several baths of high purity water, ringing residual water from the SIS sponge material between rinses.

EXAMPLE 2

An SIS sponge material in hydrated form, prepared as in Example 1, is placed between two ridged plates and compressed. The plates are clamped so that compression is maintained, and the clamped structure is lyophilized over a period of approximately 1-2 hours. The rigid plates are removed, leaving the SIS sponge material in a highly densed, compacted, flattened shape. This compacted material is highly absorbent and expandable, and can be used in a variety of medical applications. In one embodiment a sponge pellet configured for percutaneous insertion through the cannula of a catheter and/or needle is cut from the compacted SIS sponge matrix.

EXAMPLE 3

A crosslinked SIS sponge matrix, prepared as in Example 1, was swollen in a 0.9% USP saline for injection solution.

This material was used alongside a sample of GELFOAM in testing to determine the coagulation time of untreated whole human blood in the presence of the materials. The average clotting time for both materials was 8 minutes, within the normal coagulation time for human blood.

While the invention has been detailed in the foregoing description, the same is to be considered as illustrative and not restrictive in character, it being understood that only the preferred embodiment has been shown and described and that all changes and modifications that come within the spirit of the invention are desired to be protected. Further, all publications cited herein are considered indicative of the skills possessed by those in the art, and all such publications are hereby incorporated herein by reference in their entirety.

What is claimed is:

1. A method for preparing a medical device, comprising:
    forming a three-dimensionally stable sponge structure including collagen, said forming including crosslinking the collagen with a chemical crosslinking agent, and drying the sponge structure to form a dried three-dimensionally stable sponge structure;
    wetting the dried three-dimensionally stable sponge structure to form a wetted three-dimensionally stable sponge structure;
    radially compacting the wetted three-dimensionally stable sponge structure by subjecting the three-dimensionally stable sponge structure to radial compaction force, wherein said radial compaction force compacts the sponge structure radially so as to provide a generally cylindrical shape to the sponge structure and to provide a compacted volume to pores of the sponge structure;
    drying the wetted three-dimensionally stable sponge structure by lyophilization during said compacting to provide said sponge structure in a dried, compacted state having said generally cylindrical shape and having a density;
    wherein upon removal of said compaction force, said sponge structure is structurally stable and remains in said dried, compacted state having said generally cylindrical shape and having said pores stably retained at said compacted volume until said sponge structure in said dried, compacted state is contacted with a liquid susceptible to absorption by said sponge structure; and
    wherein said sponge structure in said dried, compacted state is expansible at least 100% by volume when saturated with deionized water.

2. The method of claim 1, wherein said density is at least 0.05 g/cm$^3$ on a dry weight basis.

3. The method of claim 2, wherein said density is in the range of 0.05 g/cm$^3$ to about 0.2 g/cm$^3$ on a dry weight basis.

4. The method of claim 3, wherein said density is in the range of about 0.075 g/cm$^3$ to about 0.2 g/cm$^3$ on a dry weight basis.

5. The method of claim 1, wherein said collagen is provided by an extracellular matrix.

6. The method of claim 5, wherein said extracellular matrix retains one or more native growth factors from the source tissue.

7. The method of claim 5, wherein said extracellular matrix comprises submucosa or basement membrane.

8. The method of claim 6, wherein said extracellular matrix comprises submucosa or basement membrane.

9. The method of claim 1, wherein said crosslinking comprises contacting the collagen with a chemical crosslinking agent providing polar groups in the sponge structure.

10. The method of claim 1, wherein said crosslinking agent is a polyepoxide compound.

11. The method of claim 10, wherein said polyexpoxide compound is a polyglycidyl ether compound.

12. The method of claim 11, wherein said polyglycidyl ether compound is a diglycidyl ether compound.

13. The method of claim 1, also comprising the step of providing the sponge structure in said compacted state within a cannula of a percutaneously-deliverable device.

14. The method of claim 13, wherein said percutaneously-deliverable device is a biopsy needle.

15. The method of claim 13, wherein said percutaneously-deliverable device is a catheter.

16. A medical device, comprising:
    a percutaneously-deliverable medical device having a cannula;
    a lyophilized, chemically-crosslinked sponge matrix material comprising collagen received in said cannula;
    said lyophilized sponge matrix material having been formed by providing a wetted chemically-crosslinked sponge matrix material comprising collagen in a radially compacted state in which pores of the sponge matrix material have a compacted volume, and lyophilizing the wetted chemically-crosslinked sponge matrix material while subjecting the sponge matrix material to a radial compaction force in the radially compacted state providing a generally cylindrical shape and compacted size to the sponge matrix material, with said lyophilized sponge matrix material having a compacted density and a stabilized compacted structure characterized by having been lyophilized while being subjected to the radial compaction force in the radially compacted state, wherein upon removal of said compaction force, said sponge matrix material remains at said compacted size having said pores stably retained at said compacted volume until said sponge matrix material having said stabilized compacted structure is contacted with a liquid susceptible to absorption by said sponge matrix material;
    said compacted density being at least 0.05 g/cm$^3$ on a dry weight basis;
    said lyophilized sponge matrix material in said radially compacted state being effective to expand from said compacted state when wetted so as to provide an expanded sponge matrix material having an expanded density less than said compacted density on a dry weight basis, with said expanded density in the range of about 0.01 g/cm$^3$ to about 0.1 g/cm$^3$; and
    wherein said lyophilized sponge matrix material in said radially compacted state is expansible at least 100% by volume when saturated with deionized water.

17. The medical device of claim 16, wherein said lyophilized sponge matrix material in said compacted state is in the form of a pellet having a diameter less than about 2 millimeters.

18. The medical device of claim 16, wherein said lyophilized sponge matrix material in said compacted state is expansible at least 100% by volume in less than about ten seconds when saturated with deionized water.

19. The medical device of claim 17, wherein said lyophilized sponge matrix material in said compacted state is expansible at least 100% by volume in less than about ten seconds when saturated with deionized water.

20. The medical device of claim 18, wherein said compacted density is in the range of about 0.075 g/cm$^3$ to about 0.2 g/cm$^3$ on a dry weight basis.

21. The medical device of claim 16, wherein said compacted density is in the range of 0.05 g/cm$^3$ to about 0.2 g/cm$^3$ on a dry weight basis.

22. The medical device of claim 19, wherein said compacted density is in the range of about 0.075 g/cm$^3$ to about 0.2 g/cm$^3$ on a dry weight basis.

23. The medical device of claim 16, wherein said collagen is provided by an extracellular matrix.

24. The medical device of claim 23, wherein said extracellular matrix comprises one or more growth factors from the source tissue.

25. The medical device of claim 23, wherein said extracellular matrix comprises submucosa or basement membrane.

26. The medical device of claim 24, wherein said extracellular matrix comprises submucosa or basement membrane.

27. The medical device of claim 16, wherein said sponge matrix material is crosslinked with a carbodiimide crosslinking agent.

28. The medical device of claim 16, wherein said sponge matrix material is crosslinked with a chemical crosslinking agent providing polar groups in the sponge matrix material.

29. The medical device of claim 28, wherein said crosslinking agent is a polyepoxide compound.

30. The medical device of claim 29, wherein said polyexpoxide compound is a polyglycidyl ether compound.

31. The medical device of claim 30, wherein said polyglycidyl ether compound is a diglycidyl ether compound.

32. The medical device of claim 16, wherein said percutaneously-deliverable device is a biopsy needle.

33. The medical device of claim 16, wherein said percutaneously-deliverable device is a catheter.

* * * * *